United States Patent
Hayton et al.

(10) Patent No.: US 10,463,802 B2
(45) Date of Patent: Nov. 5, 2019

(54) DRUG DELIVERY DEVICE

(71) Applicant: SANOFI-AVENTIS DEUTSCHLAND GMBH, Frankfurt am Main (DE)

(72) Inventors: Paul Hayton, Bristol (GB); James West, Bristol (GB); James Coop, Bristol (GB); Stephen Francis Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 133 days.

(21) Appl. No.: 15/576,584

(22) PCT Filed: May 24, 2016

(86) PCT No.: PCT/EP2016/061653
§ 371 (c)(1),
(2) Date: Nov. 22, 2017

(87) PCT Pub. No.: WO2016/188985
PCT Pub. Date: Dec. 1, 2016

(65) Prior Publication Data
US 2018/0193568 A1  Jul. 12, 2018

(30) Foreign Application Priority Data
May 27, 2015 (EP) .................................. 15169312

(51) Int. Cl.
*A61M 5/315* (2006.01)
*A61M 5/20* (2006.01)
*A61M 5/19* (2006.01)

(52) U.S. Cl.
CPC .......... *A61M 5/31583* (2013.01); *A61M 5/19* (2013.01); *A61M 5/2033* (2013.01);
(Continued)

(58) Field of Classification Search
CPC .. A61M 5/19; A61M 5/31583; A61M 5/2033; A61M 5/2066; A61M 5/3155;
(Continued)

(56) References Cited

U.S. PATENT DOCUMENTS

2007/0060894 A1* 3/2007 Dai ..................... A61M 5/19
604/207
2013/0253440 A1* 9/2013 Smith ............... A61M 5/31565
604/246
(Continued)

FOREIGN PATENT DOCUMENTS

EP      1603610     12/2005
GB      2488735     9/2012
(Continued)

OTHER PUBLICATIONS

International Search Report and Written Opinion in International Application No. PCT/EP2016/061653, dated Aug. 3, 2016, 9 pages.
(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

Drug delivery device comprising a housing retaining a primary drug delivery assembly for the delivery of a primary medicament with a primary dose setting member configured to rotate in a helical movement to set a dose of the primary medicament and a secondary drug delivery assembly for the delivery of a secondary medicament. A dose dial is movable between a first position and a second position in axial direction and is rotationally constrained with respect to the housing when moved from the first position into the second position and is rotationally constrained to the primary dose setting member in the second position for setting a dose of the primary medicament. A secondary drive sleeve of the secondary drug delivery assembly serves for dispense of the secondary medicament. The dose dial and the secondary drive sleeve can be coupled for dose setting.

12 Claims, 4 Drawing Sheets

(52) U.S. Cl.
CPC ........ *A61M 5/2066* (2013.01); *A61M 5/3155* (2013.01); *A61M 5/31563* (2013.01); *A61M 5/31585* (2013.01); *A61M 5/31596* (2013.01)

(58) Field of Classification Search
CPC .......... A61M 5/31563; A61M 5/31585; A61M 5/31596
See application file for complete search history.

(56) References Cited

U.S. PATENT DOCUMENTS

| | | | | |
|---|---|---|---|---|
| 2013/0261556 | A1* | 10/2013 | Jones | A61M 5/19 604/191 |
| 2013/0267908 | A1* | 10/2013 | Leak | A61M 5/19 604/191 |

FOREIGN PATENT DOCUMENTS

| | | |
|---|---|---|
| WO | WO 94/11039 | 5/1994 |
| WO | WO 2004/078241 | 9/2004 |
| WO | WO 2012/072533 | 6/2012 |

OTHER PUBLICATIONS

International Preliminary Report on Patentability in International Application No. PCT/EP2016/061653, dated Nov. 28, 2017, 7 pages.

* cited by examiner

DRUG DELIVERY DEVICE

CROSS REFERENCE TO RELATED APPLICATIONS

The present application is the national stage entry of International Patent Application No. PCT/EP2016/061653, filed on May 24, 2016, and claims priority to Application No. EP 15169312.4, filed in on May 27, 2015, the disclosures of which are expressly incorporated herein in entirety by reference thereto.

TECHNICAL FIELD

The present disclosure is directed to a drug delivery device for injecting two or more medicaments from separate medicament cartridges with a primary drug delivery assembly and a secondary drug delivery assembly.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Another example of a medicament combination is the administration of a pain reliever in combination with a medicament for treating osteoarthritis. For example, a non-adjustable fixed dose of an anesthetic could be combined with an adjustable dose of an inflammatory medicament against, e.g. rheumatoid arthritis.

Drug delivery devices of the aforementioned kind often have applications where regular injection by persons without formal medical training occurs. This is increasingly common among patients having diabetes or the like, e.g. osteoarthritis. Self-treatment enables such patients to conduct effective management of their disease.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

In combination therapy, a primary medicament and a secondary medicament are delivered in a specific relationship to deliver the optimum therapeutic dose. The injection devices of the generic kind usually comprise a housing in which two or more drug delivery assemblies are retained. Such devices include a primary drug delivery assembly for dispensing the primary medicament such as the long-acting insulin and a secondary drug delivery assembly for dispensing the secondary medicament, such as GLP-1. Some kinds of drug delivery assemblies comprise a compartment such as a cartridge holder for accommodating a replaceable medicament container such as a cartridge which stores the medicament.

In some cases, depending on the patient or the stage of the therapy, an effective treatment requires variations in the quantities and/or proportions of the medicaments making up the combined therapy. For example, the patient may require a non-adjustable fixed dose of the secondary medicament in combination with an adjustable variable dose of the primary medicament.

The effectiveness of a combined delivery of medicaments may require one or more doses to be delivered sequentially with one of the two medicaments being injected into the human body prior to the delivery of the other medicament. Such treatment may be conducted with devices that include two separate dispensing mechanisms that are actuated independently from each other such that the dispensing mechanisms are activated successively. However, such devices are difficult for users to handle.

SUMMARY

GB 2 488 735 A describes a drug delivery device for simultaneous delivery of at least two medicaments via a single dispense interface. The device comprises a dose setting mechanism, a drive mechanism and a divided spindle with a first and a second section, where the first section is operably coupled to a first cartridge containing a first medicament and where the second section is operably coupled to a second cartridge containing a second medicament, the second cartridge being arranged alongside the first cartridge. Activation of the device by a trigger forces the divided spindle in the distal direction, thereby causing the device to deliver a respective dose of the first and second medicaments. In one embodiment, rotation of a dose setter sets up a dose of the first medicament and winds up a torsional spring. A coupling has a first and a second gear. During dose setting, the gears do not rotate. During dose injection, the first gear rotates the second gear under the force of the spring and the spindle sections are driven to dispense the medicaments.

There exists a strong need to provide users of such injection devices with an easy to use device that allows safer and more convenient setting of two doses of medicaments stored in separate compartments.

Certain aspects of the subject matter described here can be implemented as a drug delivery device with the features as defined in claim 1.

The present disclosure is in particular suitable for drug delivery devices configured for replaceable cartridges. For example, by detaching the cartridge holder from the housing body, the user may replace an empty cartridge with a new one. Then the cartridge holder may be reattached to the housing body. However, the disclosure also includes disposable drug delivery devices that are usually thrown away by the user after the content of medicament cartridge has been dispensed.

Drug delivery devices of the generic kind are also called dual cartridge devices and comprise a housing retaining a primary drug delivery assembly for the delivery of a primary medicament, wherein the primary drug delivery assembly comprises a primary dose setting member such as a dosing sleeve, configured to rotate in a helical movement, usually in a first rotational direction, and to displace proximally with respect to the housing to set a dose of the primary medicament to be dispensed. The secondary drug delivery assembly serves for the delivery of a secondary medicament.

In accordance with the disclosure, the secondary drug delivery assembly comprises a drive sleeve, herein referred to as the secondary drive sleeve and a lead screw with a first and a second threaded portion, wherein the first threaded position is in threaded engagement with a thread that is fixed in the housing of the device so that rotation of the lead screw displaces the lead screw in a distal direction. At the end of the lead screw there may be provided a bearing for displacing a bung in a medicament cartridge.

The second threaded portion is in threaded engagement with an internal thread of the drive sleeve, wherein the second threaded portion is formed on flexible arms such that proximal movement of the drive sleeve causes the flexible arms to deflect, preferably, inwardly and the drive sleeve to move relative to the lead screw. When the drive sleeve is moved distally, this threaded engagement causes the lead screw to rotate and to displace distally because the flexible arms do not deflect.

The lead screw threads may be opposite hands. The interaction of the drive sleeve, the lead screw and an insert, which may be a lead screw nut, results in a mechanical reduction of the linear travel of the drive sleeve travel to the linear travel of the lead screw. The drive sleeve is designed such that it can travel axially with respect to the housing but cannot rotate. The thread at the proximal end of the lead screw is formed on the flexible arms and the thread-form of the drive sleeve with which it co-operates may be ramped on one side. To set a dose of the secondary medicament to be dispensed, the drive sleeve is moved axially in proximal direction relative to the housing. During setting, the flexible arms deflect so that the secondary drive sleeve moves proximally relative to the lead screw. The set dose of the secondary medicament is dispensed by moving the secondary drive sleeve axially in distal direction to return it to its starting position. By this action, the thread form of the drive sleeve engages the flexible arm of the lead screw and the lead screw is caused to rotate. Because the lead screw is threaded to the lead screw nut it advances through this thread to dispense the set dose of the secondary medicament. The lead screw advances by a distance that corresponds to the relationship between the leads of the first and second threads.

A dose dial is movable between a first position and a second position in axial direction with respect to the primary dose setting member, wherein the dose dial is threaded to the secondary drive sleeve such that rotation of the dose dial causes the dose dial to move relative to the secondary drive sleeve in axial direction, wherein the dose dial is configured in such way that the dose dial is rotationally constrained with respect to the housing (in the first position and) when moved from the first position to the second position in proximal direction when the primary dose setting member is in a zero unit dose position so that a dose of the secondary medicament is set and in such way that that the dose dial is rotationally constrained to the primary dose setting member in the second position and free to rotate relative to the housing so that a dose of the primary medicament is set. When a dose of the primary medicament has not been set, the primary dose setting member is in a zero unit dose position, the most distal position of the primary dose setting member. Accordingly, when the user straightly pulls the dose dial, a dose of the secondary medicament is set. When the user rotates the dose dial, a dose of the primary medicament is set.

By means of the dose dial, the user can use a pulling action to set a dose of the secondary medicament, wherein axial movement of the dose dial during that first phase does not cause any dose setting in the primary drug delivery assembly. By rotation of the dose dial in the second position, the user can set the dose of the primary medicament to be dispensed. Rotation in the second position sets a dose of the primary medicament with relative axial displacement between the dose dial and the secondary drive sleeve without affecting the axial position of the secondary drive sleeve. The dose dial may be permanently keyed to the primary dose setting member. The dose dial may also be provided with spline features such as dose that engage corresponding spline features on the primary dose setting member in second position. The secondary drive sleeve is rotationally constrained with respect to the housing and cannot rotate but displace axially with respect to the housing.

The housing may retain the drug deliver assemblies, with the drug delivery assemblies being placed next to each other. At a distal section, medicament cartridges with the two medicaments may be attached. The drug delivery assemblies respectively comprise a piston rod, a lead screw or the like configure to displace in distal direction during dispense such as to displace a bung in the respective medicament cartridge. A "2 to 1" needle adapter may be attached to the housing. In a preferred embodiment, this adapter is a disposable component; however, it is expediently designed so that it can be reused for multiple injections before it must be discarded. The delivery needle may be replaced after every injection. The delivery needle may attach to a hub that is integral to the adapter. The adapter includes two needles that are respectively configured for fluid communication with one of the two medicament cartridges and the injection needle.

A suitable drug delivery assembly that may be retained in the housing as the primary drug delivery assembly is described in EP 1 603 610 A1, which is incorporated herein by reference. In such device, modifications as described in the following are possible. The primary drug delivery assembly comprises a dose dial sleeve as dose setting member which can be coupled to the dose dial. The primary drug delivery assembly comprises a piston rod with a first threaded portion at a first (distal) end and a second threaded portion at a second (proximal) end. The first thread and the second thread are oppositely disposed. An insert is provided with a threaded insert, which is in threaded engagement with the first threaded portion of the piston rod. A drive sleeve extends about the piston rod. The drive sleeve is generally cylindrical. The drive sleeve is provided at a first (distal) end with a first radially extending flange. A second radially extending flange is provided spaced a distance along the drive sleeve from the first flange. An intermediate thread is provided on an outer part of the drive sleeve extending between the first flange and the second flange. A helical groove extends along the internal surface of the drive sleeve. The second thread of the piston rod is adapted to work within the helical groove.

A shoulder is formed between a proximal end of the drive sleeve and an extension provided at the proximal end of the drive sleeve. The extension has reduced inner and outer diameters in comparison to the remainder of the drive sleeve. A second end of the extension is provided with a radially outwardly directed flange.

A clutch is disposed about the drive sleeve, between the drive sleeve and the dose setting member, which is configured as a dose dial or dose setting sleeve. The dose dial sleeve rotates in a helical movement, a combination of rotation and axial displacement during dose setting. The dose dial sleeve is provided outside of the clutch and radially inward of the main housing. A helical groove is provided about an outer surface of the dose dial sleeve engaging a helical rib provided by the housing. The helical groove on the dose dial sleeve and the helical groove in the drive sleeve have the same lead. This allows the dose dial sleeve to extend from the main housing and the drive sleeve to climb the piston rod at the same rate The clutch is cylindrical and is provided at a distal end with a series of saw teeth. Towards the proximal end of the clutch means there is located a radially inwardly directed flange. The flange of the clutch means is disposed between the shoulder of the drive sleeve and the radially inwardly directed flange of the extension. The proximal end of the clutch means is provided with a plurality of dog teeth adapted to engage with a second end of the dose dial sleeve. The clutch is keyed to the drive sleeve by way of splines to prevent relative rotation between the clutch and the drive sleeve.

A clicker spring is located adjacent the proximal flange of the drive sleeve and splined to the housing. The clicker spring has a flexible arm extending in proximal direction, engaging the saw teeth of the clutch. A dose dial grip is secured to the dose dial sleeve to prevent relative movement therebetween. The dose dial grip is provided with a central opening. A dispense button of generally 'T' section is provided at a second end of the pen-type injector. A stem of the button may extend through the opening in the dose dial grip.

Dose setting is performed by rotation of the dose dial which rotates the dose dial sleeve. When the desired dose has been dialed, the user may then dispense this dose by de-pressing the button. The button engages and displaces the clutch axially with respect to the dose dial sleeve causing the dog teeth to disengage. However the clutch means remains keyed in rotation to the drive sleeve. The dose dial sleeve and associated dose dial grip are now free to rotate (guided by the helical rib located in helical groove).

The axial movement deforms the flexible arm of the clicker spring and ensures that the saw teeth cannot be overhauled during dispense. This rotationally locks the clutch to the main housing and prevents the drive sleeve from rotating with respect to the main housing though it is still free to move axially with respect thereto. This deformation is subsequently used to urge the clutch back into proximal direction to restore the connection between the clutch and the dose dial sleeve when pressure is removed from the button.

The longitudinal axial movement of the drive sleeve causes the piston rod to rotate through the opening in the insert, thereby to advance the piston in the cartridge. In the sense of the disclosure, the dial grip of the above described drug delivery assembly may form the respective dose setting member. Of course, the dose dial may also form the primary dose setting member.

According to a further embodiment of the disclosure, the dose dial is configured as a sleeve at least partly surrounds the primary dose setting member.

According to a further embodiment of the disclosure, primary dose setting member is in threaded engagement with a thread provided in the housing or on an insert, which has the same lead as the thread engagement between the secondary drive sleeve and the dose dial.

According to a further embodiment of the disclosure, the dose dial is axially splined to the housing in the first position and is splined to the primary dose setting member in the second position.

For determining a fixed dose that cannot be influenced by the user in the combined therapy treatment, a stop may be provided to limit the axial travel of the secondary drive sleeve in proximal direction, wherein the secondary drive sleeve reaches the stop when the dose dial reaches the second position.

In order to prevent the delivery of the secondary medicament until a dose of the primary medicament has been set, a further embodiment of the disclosure comprises a locking element configured to engage the secondary drive sleeve when the dose dial is moved from the first into the second position relative to the primary dose setting member such that movement of the secondary drive sleeve in distal direction is prevented, wherein the dose dial prevents the locking element from disengaging from the secondary drive sleeve, wherein the dose dial is configured such rotation of the dose dial in the second position to set a dose of the primary medicament allows the locking element to disengage from the drive sleeve such that displacement of the drive sleeve in distal direction is allowed.

The locking element may be configured as a flexing rib provided in the housing configured to engage a distally oriented surface of the secondary drive sleeve such that movement of the secondary drive sleeve in distal direction is prevented, According to a further embodiment, the drive sleeve has a slanted surface configured to deflect the flexing rib so that the secondary drive sleeve is free to move distally, wherein in the second position of the dose dial, the dose dial prevents the flexing rib from deflecting until the dose dial has been rotated. Starting rotation of the dose dial to set a dose of the primary medicament may allow the flexible rib to deflect.

According to a further embodiment of the disclosure, the dose dial is splined to a rib provided in the housing until the dose dial has been moved from the first into the second position. This rib prevents rotation of the dose dial and consequently the setting of a dose of the primary medicament. Thus, the user actions always include to the setting of a dose of the secondary medicament. A flexing arm on the dose dial may engage a rib in the housing to lock the dose dial against rotation, wherein the dose dial disengages from the rib in the second position.

According to a further embodiment of the disclosure, the primary dose setting member is configured to move in distal direction in a helical movement during dispense of the primary medicament, wherein the dose dial is configured to reengage with the rib after dispense of the primary medicament. For this purpose, the dose dial may have a flexible element that engages the rip in a snapping action, Thereby, after dispense, the device is again in the condition which requires the user to pull the dose dial.

According to a further embodiment of the disclosure, the drug delivery device comprises a dose button arranged in the dose dial in such way that displacement of the dose button in distal direction causes the dose dial to move in distal direction from the second into the first position such that a set dose of the secondary medicament is dispensed and in such way that when the dose dial is in the first position, the dose button engages a dispense button of the primary drug delivery assembly such that further movement of the dose button in distal direction causes a set dose of the primary medicament to be dispensed.

According to a further embodiment, the drug delivery device comprises a primary medicament cartridge and a secondary medicament cartridge, wherein the primary medicament cartridge is coupled to the primary drug delivery assembly and the secondary medicament cartridge is coupled to the secondary drug delivery assembly, and wherein the primary and the secondary medicament cartridge contain a medicament. The cartridges may be accommodated in an at least partly transparent cartridge holder.

According to a further embodiment of the disclosure, the drug delivery device is configured as a disposable device.

The primary dose setting member may be configured as a number sleeve with a dose scale provided thereon. For indicating the set doses, the number sleeve dose scale may incorporate two number rows with one number row indicating the set dose of the primary medicament and with the other number row indicating the set dose of the secondary medicament.

The device efficiently prevents mono-dosing of the primary and of the secondary medicament and ensure that the patient receives a fixed dose of the secondary medicament before the primary medicament can be administered.

The device efficiently facilitates that the medicaments are administered one after the other thus preventing mixing with one another. This ensures that each medicament provides its intended effect alone without interacting with each other.

The effect that the non-adjustable fixed dose is administered before the adjustable dose is particularly beneficial for example when a non-adjustable fixed dose of an anesthetic is administered to provide pain relief and is combined with an adjustable dose of an inflammatory medicament against, e.g. rheumatoid arthritis. Thus the painful administration of a medicament can be mitigated with administering a local anesthetic beforehand. Another example would be a combination therapy for patients suffering from diabetes that require a fixed dose of a GLP-1 and an individual dose of a long-acting insulin in a combination therapy.

The term "medicament", as used herein, means a pharmaceutical formulation containing at least one pharmaceutically active compound,
wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF FIGURES

Non-limiting, an exemplary embodiment of the disclosure will now be described with reference to the accompanying drawings, in which.

DETAILED DESCRIPTION

Figure 1:
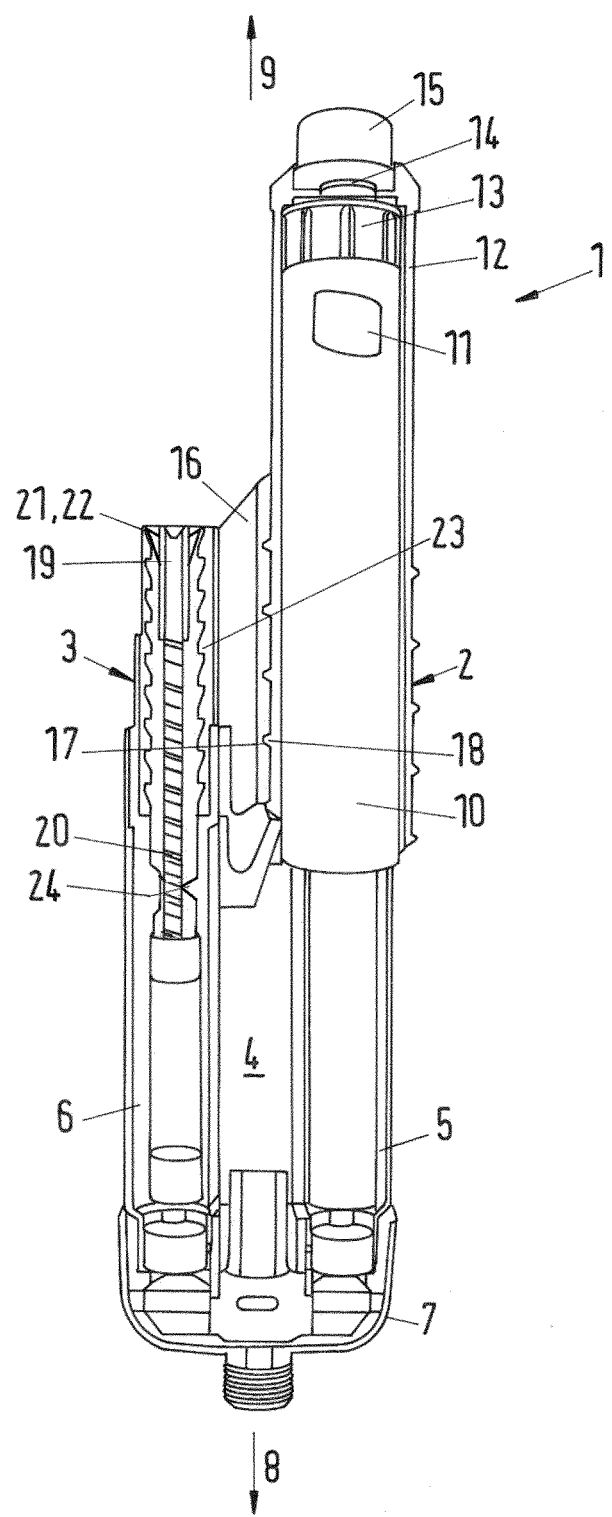
FIG. 1 shows a the dual cartridge drug delivery device in accordance with a first embodiment of the disclosure view with parts removed.

FIG. 1 shows the interior of a drug delivery device 1 comprising a primary drug delivery assembly 2 and a secondary drug delivery assembly 3, both retained in a housing that is only indicated by reference numeral 4. The primary drug delivery assembly 2 serves for the delivery of a primary medicament contained in a primary cartridge 5. The secondary drug delivery assembly 3 serves for the delivery of a secondary medicament contained in a secondary cartridge 6. The cartridges may also be retained in a cartridge holder that is attachable to the distal end of the device 1. The cartridge holders for the cartridges may be integrated in a single cartridge holder hub.

At the distal end of the assembly, a 2-1 needle adapter 7 is attached. At the distal end 8 of the needle adaptor 7 a screw thread is formed. An injection needle can be attached to said screw thread or injection. The injection needle is in fluid communication with two proximally oriented needles in the needle adapter 7 that pierce the respective septa of the respective medicament cartridge 5 and 6. The device 1 extends from the distal end 8 to a proximal end 9.

The primary drug delivery assembly 2 comprises a primary housing, housing body or housing section 10, a primary dose setting member 11 in the form of a dose dial sleeve, which is threadedly engaged with a threaded insert (not shown) fixed in the primary housing section 10 so that when the primary dose setting member 11 is rotated, it moves along a helical pattern in axial direction. The primary dose setting member 11 is connected to a dose dial 12 via a connection element 13, which is a dial grip of a regular drug delivery device. The dose dial 12 is configured as a dial collar and assembles as a sleeve over the primary drug delivery assembly 2.

The dose 12 is movable between a first distal axial position and a second proximal axial position. The dose dial 12 is rotationally constrained with respect to the housing 4 when in the first position and when the dose setting member 11 is in its most distal position, which corresponds to a set dose of zero units.

When the dose dial 12 is moved proximally in axial direction, it disengages from the rotational lock with the housing 4 so that the dose dial 12 is free to rotate relative to the housing 4. The dose dial 12 is rotationally constrained to the primary dose setting member 11. The dose dial 12 may be permanently splined to the primary dose setting member by an axially extending spline connection. Rotation of the dose dial 12 is transferred to the primary dose setting member 11. The primary dose setting member 11 is usually rotated (in a first rotational direction) to set an increasing dose of the primary medicament. When the dose dial 12 is in the second position, a dose of the primary medicament can be set by rotating the dose dial 12. In this case the dose dial 12 and the primary dose setting member 11 displace in proximal direction in a helical movement.

Inside the primary drug delivery assembly 2, there is a dose dispense mechanism including a clutch, a piston rod and a drive sleeve. For dispense of the primary medicament, a dispense button located in the connection element 13 is pressed. In the embodiment shown, a spring 14 urges a dose button 15 in the dose dial 12 in proximal direction away from a dispense button (not shown) of the primary drug delivery assembly.

When a dose of a primary medicament has been set, the dose button 15 is pressed so that the dose button acts on the dispense button of the primary drug delivery assembly. The dispense button acts on the clutch mechanism between the primary drive sleeve and the primary dose setting member 11 which is disengaged and the primary dose setting member 11 is forced to move in distal direction in a pure axial motion thereby rotating the piston rod located inside. As the piston rod is in threaded engagement with a housing insert, the piston rod displaces in distal direction thereby displacing a bung in the cartridge 5.

In order to seta dose, the user is forced to follow specific steps. As the dose dial 12 is blocked rotationally within the housing 4 until it is pulled upwards (proximally) from the first position into the second position relative to the primary dose setting member 11, the user has to pull the dose dial 12 in proximal direction. That causes the engagement with the housing 4 to be removed. Thereafter, the dose dial 12 can be rotated wherein this rotation is transmitted to the primary dose setting member 11 such that a dose of the primary medicament is set.

The secondary drive sleeve 16 has a thread 17 extending in axial direction and engaged by an outer thread 18 of the dose dial 12. Further the secondary drive sleeve 16 is guided axially in the housing 4 but cannot rotate. When the dose dial 12 is pulled in proximal direction, the secondary drive sleeve 16 moves with the dose dial 12 by virtue of its threaded engagement in proximal direction.

The secondary drive sleeve 16 surrounds a lead screw 19 of the secondary drug delivery assembly 2. The lead screw 19 has two threads 20, 21. The first thread 20 extends along the lead screw 19 and is in threaded engagement with thread 24 fixed in the housing 4. The second thread 21 at the proximal end of the lead screw 19 is formed on flexible arms 22 and the inner thread-form 23 of the drive sleeve 16 with which it co-operates is ramped on one side.

When the secondary drive sleeve 16 is moved proximally 9 to set a dose of the secondary medicament to be dispensed, the flexible arms 22 deflect so that the secondary drive sleeve 16 moves proximally relative to the lead screw 19. The set dose of the secondary medicament is dispensed by moving the secondary drive sleeve 16 axially in distal direction to return it to its starting position. By this action, the thread form 23 of the drive sleeve 16 engages the flexible arm 22 of the lead screw 19 and the lead screw 19 is caused to rotate. Because the lead screw 19 is threaded to the housing it advances through this thread to dispense the set dose of the secondary medicament. The lead screw advances by a distance that corresponds to the relationship between the leads of the first and second threads 20, 21.

The mechanism requires a pull-to-activate user step of the dose dial 12 (pure axial motion of the dose dial 12) which forces the secondary drive sleeve 16 to move in proximal direction such that a dose of the secondary medicament is set. Axial travel of the secondary drive sleeve is limited by a stop (not shown). When the dose dial 12 reaches its second position, the dose dial 12 is free to rotate and the stop limits the displacement of the secondary drive sleeve 16. The user is now allowed to rotate the dose dial 12 to set an increasing dose of the primary medicament. Rotation of the dose dial 12 does not cause displacement of the secondary drive sleeve 16 so that there is no further dose setting in the secondary drug delivery assembly 3.

For dispense, the user depresses the dose button 15. The depression of the dose button 15 displaces the dose dial 12 and in turn the secondary drive sleeve 16 in distal direction. The spring 14 that urges the dose button 15 in proximal direction applies a force that is stronger than a force that is required to displace the secondary drive sleeve 16. Proximal movement of the secondary drive sleeve 16 in distal direction causes the lead screw 19 of the secondary drug delivery assembly 3 to move distally such that the secondary medicament is dispensed.

After dispense of the secondary medicament, the dose button 15 reaches the primary dispense button. Then the secondary drive sleeve 16 in its original initiate position. The dose button 15 engages the primary dispense button and initiates dispense of the primary medicament by declutching the clutch inside the primary drug delivery assembly 2. Further displacement of the dose dial 12 by depressing the dose button 15 causes the primary dose setting member 11 to rotate back in distal direction thereby dispensing the primary medicament. Accordingly, the fixed dose of the secondary medicament is dispensed prior to the variable dose of the primary medicament.

Figure 2:
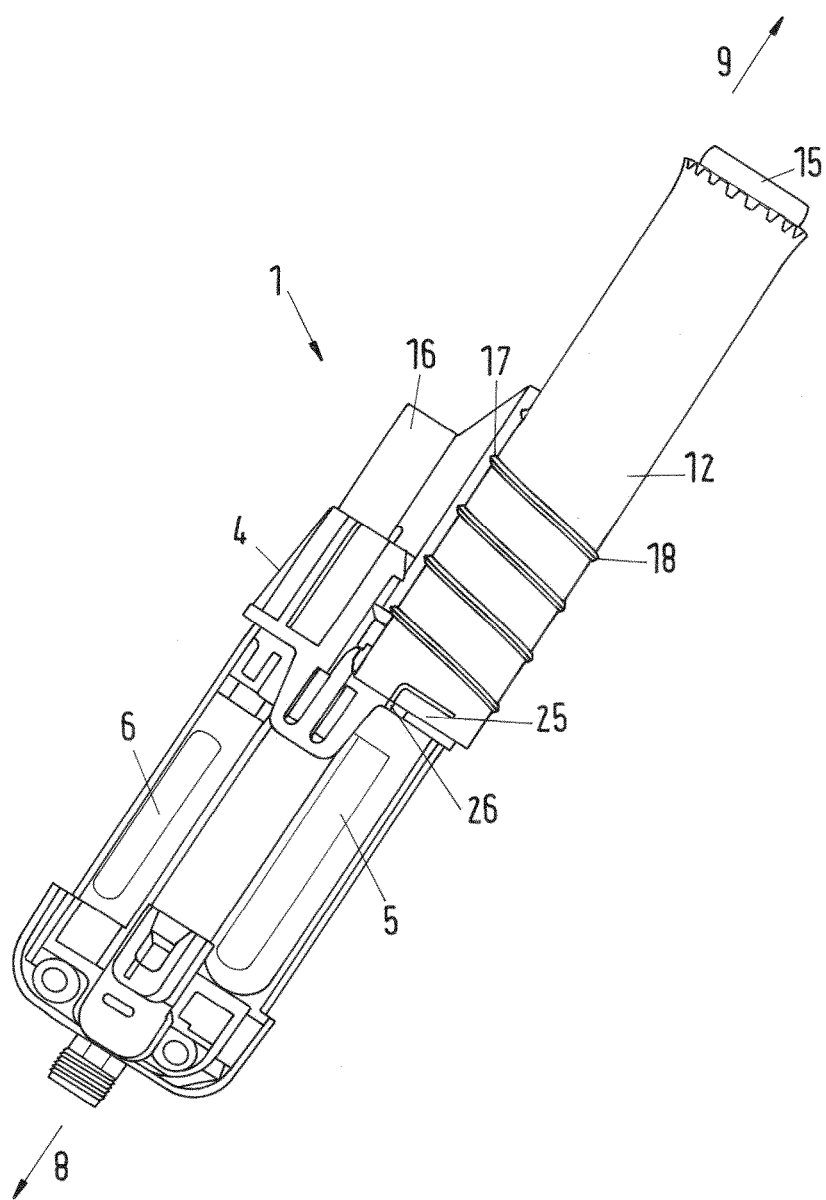
FIG. 2 a perspective view of a further embodiment of the disclosure.

FIG. 2 shows a further embodiment of the drug delivery device 1 prior to setting the doses of the primary medicament in the primary cartridge 5 and the secondary medicament in the secondary cartridge 6. In FIG. 2, merely a section of a fixed housing section is indicated with reference numeral 4. The dose dial 12 is provided with a number of numerals on an outer peripheral surface for indicating the set dose of the primary medicament which can be chosen by the user, wherein the dose of the secondary medicament is a fixed dose. At the distal end of the dose dial 12, the dose dial 12 has a flexible arm 25 that engages an axially extending rib 26 on the housing 4. The engagement between the flexible arm 25 and the rib 26 locks the dose dial against rotation. To disengage the flexible arm 25 from the rib 26, the user has to pull the dose dial 12 in proximal direction 9.

Figure 3:
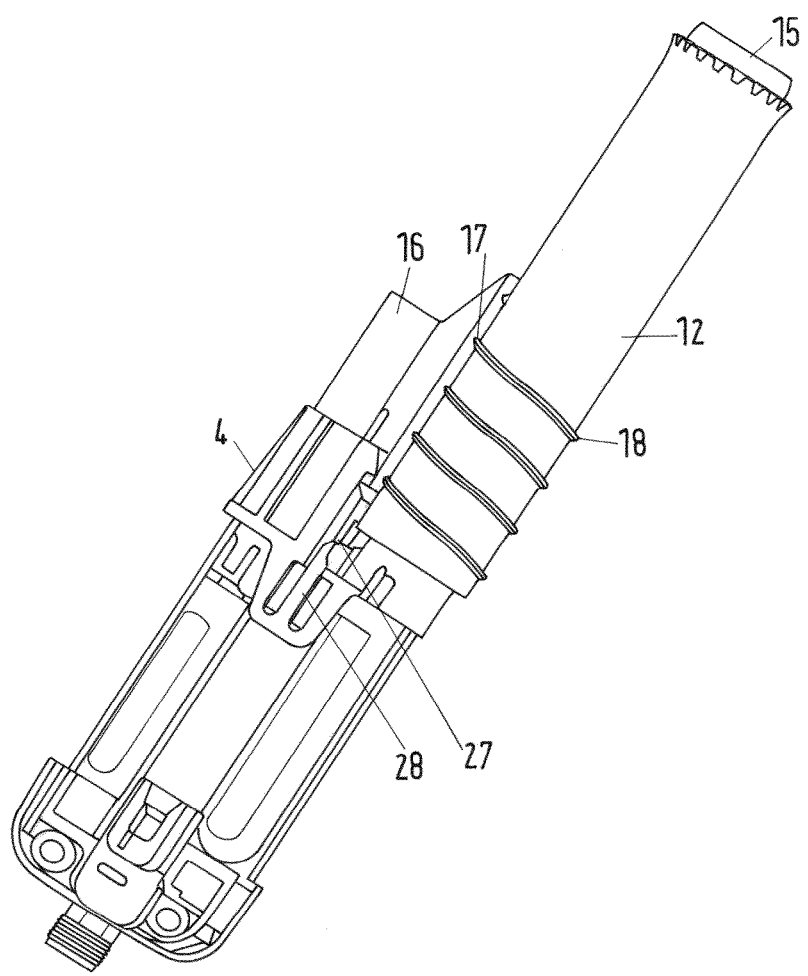
FIG. 3 the device in FIG. 2 during dose setting.

FIG. 3 shows the state of the device after the user has pulled the dose dial 12 into its second position. The flexible arm 25 has disengaged from the rib 26 and the user has begun to rotate the dose dial 12 to set an increasing dose of the primary medicament. Because of the thread engagement 17/18, when the user pulls the dose dial 12 in a pure axial motion into the second position, the secondary drive sleeve 16 is pulled proximally against a stop thereby setting a fixed dose of the secondary medicament. By rotation of the dose dial 12, the dose of the primary medicament is set. Due to the thread engagement 17/18, the dose dial 12 displaces proximally relative to the secondary drive sleeve 16 without further dose setting of the secondary medicament.

Figure 4:
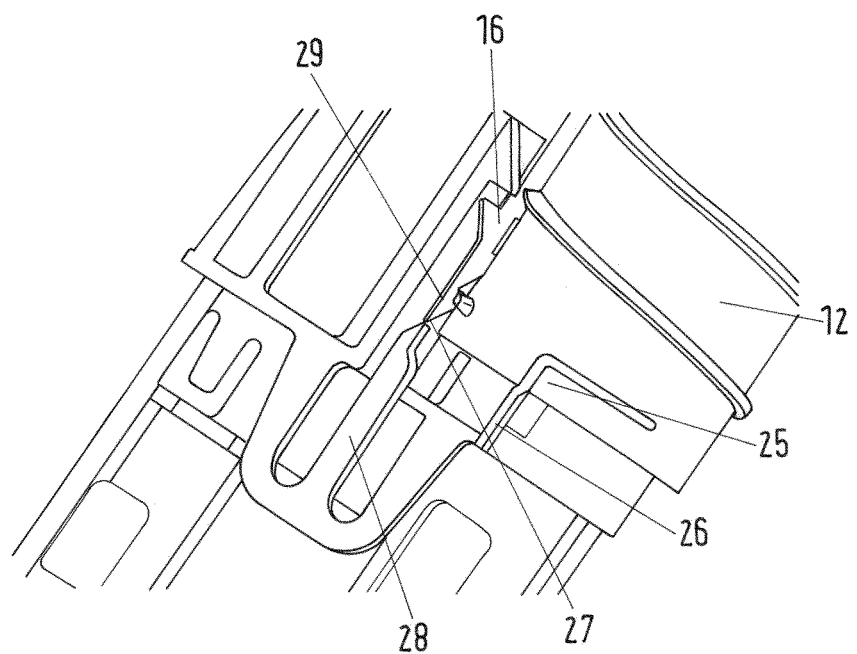

A distal section of the drive sleeve 16 has a distally oriented surface 27 configured for engagement with a locking element 28 in the form of a flexing rib provided by the housing 4. FIG. 4 shows the section with the flexing rib 28 with the dose dial 12 in the second position (disengaged from rib 26) but where the dose dial 12 has not been rotated yet to set a dose of the primary medicament. Proximal movement of the secondary drive sleeve 16 causes the flexing rib 28 to engage underneath the surface 27. The surface 27 has a slanted surface 29. The slanted surface 29 causes the flexing rib 28 to deflect toward the rib 26. When the dose dial 12 has not been rotated in this situation, the flexing rib 28 is not allowed to deflect and the secondary drive sleeve 16 cannot be displaced distally. Thus, before a set dose of the secondary medicament can be dispensed, the user is required to set a dose of the primary medicament. In turn, as the user is required to pull the dose dial 12 before he is able to set a dose of the primary medicament, the user always receives a fixed dose of the secondary medicament in combination with a variable dose of the primary medicament.

REFERENCE NUMERALS 1 drug delivery device
2 primary drug delivery assembly
3 secondary drug delivery assembly
4 housing
5 primary cartridge
6 secondary cartridge
7 needle adapter
8 distal end
9 proximal end
10 primary housing
11 primary dose setting member (primary dose dial sleeve)
12 dose dial
13 connection element
14 spring
15 dose button
16 secondary drive sleeve
17 thread
18 outer thread
19 lead screw
20 second thread
21 first thread
22 flexible arm
23 inner thread on secondary drive sleeve
24 thread on housing
25 flexing arm
26 rib
27 distally oriented surface
28 locking element (flexing rib)
29 slanted surface

The invention claimed is:

1. A drug delivery device comprising:
a housing retaining a primary drug delivery assembly for the delivery of a primary medicament, wherein the primary drug delivery assembly comprises:
a primary dose setting member configured to rotate in a helical movement to set a dose of the primary medicament, and
a secondary drug delivery assembly for the delivery of a secondary medicament, wherein the secondary drug delivery assembly comprises:
a secondary drive sleeve, and
a lead screw with a first threaded portion and a second threaded portion, wherein the first threaded portion is in threaded engagement with a thread fixed in the housing, wherein rotation of the lead screw displaces the lead screw in a distal direction, wherein the second threaded portion is in threaded engagement with an internal thread of the secondary drive sleeve , and wherein the second threaded portion is formed on flexible arms, wherein proximal movement of the secondary drive sleeve causes the flexible arms to deflect and the secondary drive sleeve to move relative to the lead screw, and wherein movement of the secondary drive sleeve in the distal direction causes the lead screw to rotate and to displace in the distal direction; and a dose dial movable between a first position and a second position in an axial direction with respect to the primary dose setting member, wherein the dose dial is configured to be rotationally constrained with respect to the housing when moved from the first position into the second position when the primary dose setting member is in a zero unit dose position, wherein the dose dial is configured to be rotationally constrained to the primary dose setting member in the second position and is free to rotate relative to the housing so that a dose of the primary medicament is set, and wherein the dose dial is threaded to the secondary drive sleeve, wherein movement of the dose dial from the first into the second position sets a dose of the secondary medicament, and wherein rotation of the dose dial in the second position causes the dose dial to move relative to the secondary drive sleeve.

2. The drug delivery device according to claim 1, wherein the primary dose setting member is in threaded engagement with a thread provided in the housing which has the same lead as the thread engagement between the secondary drive sleeve and the dose dial.

3. The drug delivery device according to claim 1, wherein a stop is provided to limit an axial travel of the secondary drive sleeve in a proximal direction, wherein the secondary drive sleeve reaches the stop when the dose dial reaches the second position.

4. The drug delivery device according to claim 1, comprising a locking element configured to engage the secondary drive sleeve when the dose dial is moved from the first into the second position relative to the primary dose setting member such that movement of the secondary drive sleeve in distal direction is prevented, wherein the dose dial prevents the locking element from disengaging from the secondary drive sleeve, and wherein rotation of the dose dial in the second position to set a dose of the primary medicament allows the locking element to disengage from the secondary drive sleeve such that displacement of the secondary drive sleeve in the distal direction is allowed.

5. The drug delivery device according to claim 4, wherein the locking element comprises a flexing rib provided in the housing, wherein the secondary drive sleeve has a slanted surface configured to deflect the flexing rib, wherein, in the second position of the dose dial, the dose dial prevents the flexing rib from deflecting until the dose dial has been rotated.

6. The drug delivery device according to claim 1, wherein the dose dial is splined to a rib provided in the housing until the dose dial has been moved from the first into the second position.

7. The drug delivery device according to claim 6, wherein the primary dose setting member is configured to move in distal direction in a helical movement during dispense of the primary medicament, wherein the dose dial is configured to reengage with the rib after dispense of the primary medicament.

8. The drug delivery device according to claim 1, comprising a dose button arranged in the dose dial, wherein displacement of the dose button in the distal direction causes the dose dial to move in the distal direction from the second position into the first position such that a set dose of the secondary medicament is dispensed, wherein, when the dose dial is in the first position, the dose button engages a dispense button of the primary drug delivery assembly such that further movement of the dose button in the distal direction causes a set dose of the primary medicament to be dispensed.

9. The drug delivery device according to claim 1, comprising a primary medicament cartridge and a secondary medicament cartridge, wherein the primary medicament cartridge is coupled to the primary drug delivery assembly and the secondary medicament cartridge is coupled to the secondary drug delivery assembly, and wherein the primary medicament cartridge and the secondary medicament cartridge respectively contain a medicament.

10. The drug delivery device according to claim 1, wherein the drug delivery device is configured as a disposable device.

11. The drug delivery device according to claim 1, wherein the dose dial is configured as a sleeve at least partly surrounding the primary dose setting member.

12. The drug delivery device according to claim 1, wherein the secondary drive sleeve is rotationally constrained with respect to the housing and cannot rotate but can displace axially with respect to the housing.

* * * * *

UNITED STATES PATENT AND TRADEMARK OFFICE
CERTIFICATE OF CORRECTION

PATENT NO. : 10,463,802 B2
APPLICATION NO. : 15/576584
DATED : November 5, 2019
INVENTOR(S) : Paul Hayton et al.

Page 1 of 1

It is certified that error appears in the above-identified patent and that said Letters Patent is hereby corrected as shown below:

In the Specification

Column 1, Line 9, under "CROSS REFERENCE TO RELATED APPLICATIONS", after "filed", delete "in"

In the Claims

Column 15, Line 7, delete "sleeve ," and insert -- sleeve, --

Signed and Sealed this
Fourteenth Day of January, 2020

Andrei Iancu
*Director of the United States Patent and Trademark Office*